United States Patent [19]

Franke

[11] Patent Number: 4,562,134
[45] Date of Patent: Dec. 31, 1985

[54] ELECTROPHOTOGRAPHIC MATERIAL WITH CYANINE SENSITIZER WITH BETAINE GROUP

[75] Inventor: Werner Franke, Wiesbaden, Fed. Rep. of Germany

[73] Assignee: Hoechst Aktiengesellschaft, Frankfurt am Main, Fed. Rep. of Germany

[21] Appl. No.: 614,823

[22] Filed: May 29, 1984

[30] Foreign Application Priority Data

May 31, 1983 [DE] Fed. Rep. of Germany ....... 3319654

[51] Int. Cl.$^4$ .............................................. G03G 5/09
[52] U.S. Cl. .................................................... 430/83
[58] Field of Search .................................. 430/82, 83

[56] References Cited

U.S. PATENT DOCUMENTS

| | | | |
|---|---|---|---|
| 3,796,573 | 3/1974 | Jones | 430/83 X |
| 3,881,926 | 5/1975 | Ohlschlager et al. | 430/83 X |
| 3,958,991 | 5/1976 | Jones et al. | 96/1.6 |
| 4,063,948 | 12/1977 | Lind | 430/83 |
| 4,218,247 | 8/1980 | Hara et al. | 430/83 X |

FOREIGN PATENT DOCUMENTS

| | | |
|---|---|---|
| 1058836 | 11/1959 | Fed. Rep. of Germany . |
| 2137325 | 1/1972 | Fed. Rep. of Germany ........ 430/82 |
| 3141554 | 5/1982 | Fed. Rep. of Germany . |
| 54-121739 | 9/1979 | Japan ..................................... 430/83 |
| 54-121740 | 9/1979 | Japan ..................................... 430/83 |

OTHER PUBLICATIONS

Res. Discl. 10015, Aug. 1972, pp. 49-51.

*Primary Examiner*—Roland E. Martin
*Attorney, Agent, or Firm*—Schwartz, Jeffery, Schwaab, Mack, Blumenthal & Evans

[57] ABSTRACT

The present invention discloses an electrophotographic recording material comprising an electrically conductive support and at least one photoconductive layer which comprises an organic photoconductor, for example, oxazole derivatives or oxadiazole derivatives, a sensitizing dye, a binder, and customary additives. The sensitizing dye contained in the photoconductive layer comprises a compound corresponding to the general formula

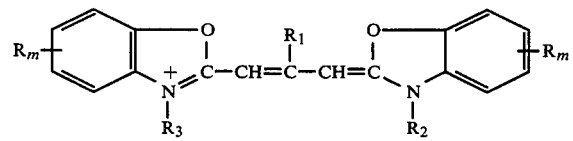

wherein
R is chlorine or bromine,
m is 1 or 2,
$R_1$ is an alkyl group having from 1 to 3 carbon atoms,
$R_2$ is $-(CH_2)_n-SO_3H$ or $-(CH_2)_2-COOH$,
$R_3$ is $-(CH_2)_n-SO_3-$ or $-(CH_2)_2-COO-$ and
n is 3 or 4.

13 Claims, 6 Drawing Figures

ELECTROPHOTOGRAPHIC MATERIAL WITH CYANINE SENSITIZER WITH BETAINE GROUP

BACKGROUND OF THE INVENTION

The present invention relates to an electrophotographic recording material comprising an electrically conductive support and at least one photoconductive layer which comprises an organic photoconductor, a sensitizing dye, a binder, and customary additives.

German Pat. No. 1,058,836 corresponding to U.S. Pat. No. 3,189,447) discloses the use of organic photoconductors in an electrophotographic reproduction process. These organic photoconductors generally have a spectral sensitivity in the long-wave ultraviolet spectral region from about 350 to 450 nm.

In order to extend the range of spectral sensitivity to about 650 nm, it is known to use sensitizers comprising a wide variety of dyes of different chemical types. A list of dyes which are effective for this purpose appears, for example, in Schultz' Dye Tables (7th edition, volume 1, 1931), which includes:
Triarylmethane dyes, for example,
  Brilliant Green (No. 760, page 314),
  Victoria Blue B (No. 822, page 347),
  Methyl Violet (No. 783, page 327),
  Crystal Violet (No. 785, page 329), and
  Acid Violet 6B (No. 831, page 351);
xanthene dyes, i.e., rhodamines, for example,
  Rhodamine B (No. 864, page 365),
  Rhodamine 6G (No. 866, page 366),
  Rhodamine G Extra (No. 865, page 366),
  Sulforhodamine B (No. 863, page 364), and
  Fast Acid Eosin G (No. 870, page 368),
and phthaleins, for example,
  Eosin S (No. 883, page 375),
  Eosin A (No. 881, page 374),
  Erythrosin (No. 886, page 376),
  Phloxin (No. 890, page 378),
  Bengal Rose (No. 889, page 378), and
  Fluorescein (No. 880, page 373);
thiazine dyes, for example
  Methylene Blue (No. 1038, page 449);
acridine dyes, for example,
  Acridine Yellow (No. 901, page 383),
  Acridine Orange (No. 908, page 387), and
  Trypaflavin (No. 906, page 386);
quinoline dyes, for example,
  Pinacyanol (No. 924, page 396), and
  Cryptocyanine (No. 927, page 397);
quinone dyes and ketone dyes, for example,
  Alizarin (No. 1141, page 449),
  Alizarin Red S (No. 1145, page 502), and
  Quinizarin (No. 1148, page 504); and cyanine dyes.

Sensitizing dyes of the aforementioned type are described in detail in German Pat. No. 2,608,082 (corresponding to U.S. Pat. No. 4,218,247).

German Pat. No. 1,904,629 (corresponding to U.S. Pat. No. 3,560,207) discloses an electrophotographic recording material containing an organic photoconductor in its photoconductive layer. The organic photoconductor is chemically activated and optically sensitized beyond the visible spectral region, by the addition of cyanine dyes which may contain substituents comprising, for example, unsubstituted or substituted thiazole, oxazole, selenazole, thiazoline, pyridine, quinoline, 3,3-dialkylindolenine, imidazole, imidazo(4,5-quinoxaline, 3,3-dialkyl-3H-pyrrolo(2,3-b)pyridine, or thiazolo(4,5-b)quinoline groups.

German Pat. No. 2,526,720 (corresponding to U.S. Pat. No. 4,063,948) discloses an electrophotographic recording material with an electrically conductive support, which is used to produce printing forms or printed circuits and is sensitized with cyanine dyes corresponding to the general formula

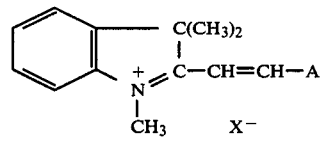

wherein
  A is an unsubstituted or substituted indolyl group, an unsubstituted or substituted benzothiazolyl-amino group, an unsubstituted or substituted phenylamino group, or an unsubstituted or substituted indolinyl group, and
  $X^-$ is a monovalent anion.

The sensitivity of the photoconductors is based, in principle, on the fact that the light energy which is available in the longer-wavelength region is absorbed by the sensitizing dyes and transferred to the photoconductor molecule.

Spectral sensitizations which result from the use of these sensitizing dyes often have the disadvantage, however, that they have a very wide sensitivity base. Recording materials prepared with the use of these dyes thus cannot be safely handled in the darkroom. This problem is particularly evident in the sensitizing dyes according to U.S. Pat. No. 4,334,001.

Use of these sensitizing dyes has the additional disadvantage that they sometimes possess several sensitization peaks and/or there is no pronounced sensitization peak at all. Frequently, the sensitization peak is not in the region of the strongest emission of the light source used for exposure, which is of critical importance, for example, in a recording material which is to be exposed to laser radiation. In addition, the spectral photosensitivity may often be increased, but the overall sensitivity is reduced or is not improved. These sensitizing dyes also often severely stain the photoconductive layer, which is inconvenient in some fields of application.

SUMMARY OF THE INVENTION

It is, therefore, an object of the present invention to provide a sensitizing dye which may be safely handled in the darkroom due to a steep drop of spectral photosensitivity towards the longer-wavelength region.

It is another object of the present invention to provide a sensitizing dye which exhibits a pronounced sensitivity peak in the region of from about 500 to 520 nm and imparts an intensive spectral photosensitivity to a photoconductive layer.

Still another object is to provide a sensitizing dye as above, which does not stain the photoconductive layer.

Yet another object is to provide a sensitizing dye which can be combined with other known dyes to produce an admixture comprising two distinct sensitivity peaks with a region of greatly reduced sensitivity therebetween.

In accomplishing the foregoing objects, there has been provided in accordance with the present invention an electrophotographic recording material, comprising an electrically conductive support layer having at least one photoconductive layer applied thereto which comprises an organic photoconductor, at least one sensitizing dye having the desired characteristics, a binder, and customary additives. A first and second sensitizing dye may be provided, such that the sensitivity peak of the second dye is shifted by more than about 60 nm in the longer-wavelength direction from the sensitivity peak of the first sensitizing dye, and a region of reduced sensitivity is formed inbetween.

Further objects, features and advantages of the present invention will become apparent from the detailed description of preferred embodiments which follows, when considered together with the attached figures of drawing.

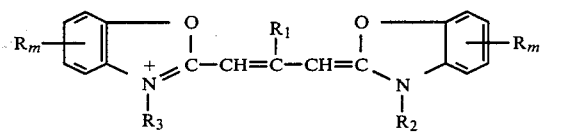

1

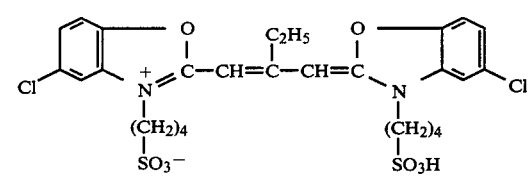

2

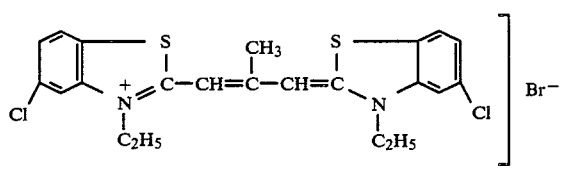

3

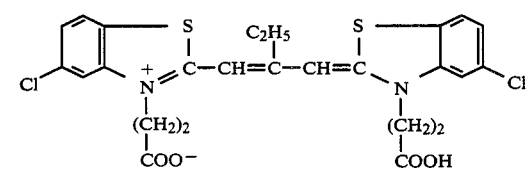

4

DETAILED DESCRIPTION OF PREFERRED EMBODIMENTS

Figure 1:
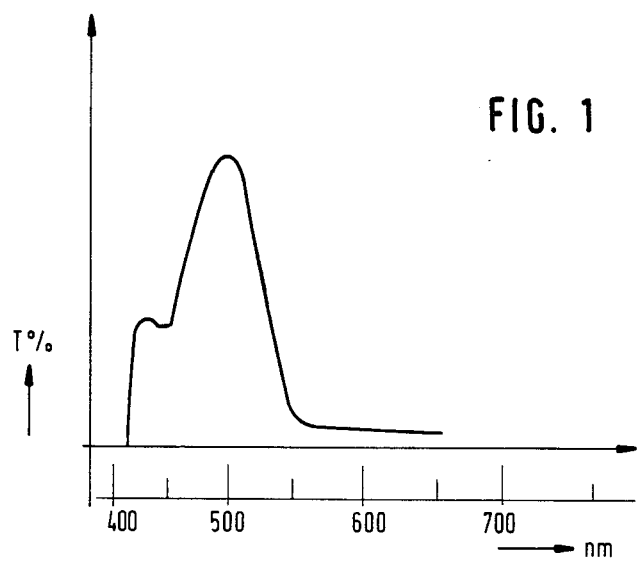
FIG. 1 shows the spectral sensitivity peak of a printing plate produced in accordance with the present invention.

An electrophotographic recording material comprises an electrically conductive support and at least one photoconductive layer which comprises an organic photoconductor, a sensitizing dye, a binder, and customary additives. The electrophotographic recording material of the present invention is characterized in that the sensitizing dye contained in the photoconductive layer comprises a compound corresponding to the formula:

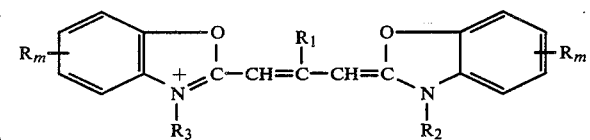

wherein
R is chlorine or bromine,
m is 1 or 2,
$R_1$ is an alkyl group having from 1 to 3 carbon atoms,
$R_2$ is —$(CH_2)_n$—$SO_3H$ or —$(CH_2)_2$—COOH,
$R_3$ is —$(CH_2)_n$—$SO_3^-$ or —$(CH_2)_2$—$COO^-$ and
n is 3 or 4.

Preferably, the sensitizing dye contained in the photoconductive layer is a compound corresponding to the following formula:

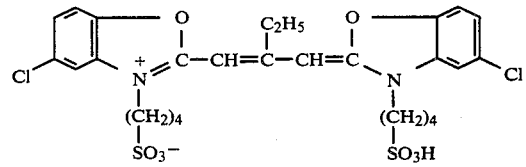

A recording material for electrophotographic reproduction produced in accordance with the present invention can be safely handled in green, yellow and red safelights, and possesses a sharply pronounced selective sensitization having a peak at from about 505 to 510 nm. In addition, the sensitization spectrum of this material shows a very steep drop toward the longer-wavelength region of the spectrum.

Recording materials can also be produced which contain the sensitizing dye of the present invention in admixture with other readily compatible selectively-acting sensitizing dyes. Dyes may be chosen to produce an admixture comprising two selective sensitizations, the peaks of which are more than about 60 nm apart from each other and are separated by a gap. Moreover, panchromatic sensitization can be achieved, by admixing sensitizing dyes which sensitize in the longer-wavelength spectral region.

Many cyanine dyes, known from photography, are capable of effecting a good spectral sensitization of silver halide. In contrast, sensitization is often only slight or nonexistent when these dyes are used for electrophotographic recording materials which contain organic photoconductors.

It was therefore unexpected that the sensitizing dye of the present invention produces a good and selective sensitization of the photoconductive layer.

One preferred embodiment of the present invention, illustrated by Formula 2 in the attached table of formulae, is distinguished by an intensive and narrow spectrum of sensitization which shows an acute peak at from about 505 to 510 nm, a slight shoulder of sensitization at about 480 nm and a very steep drop toward the longer-wavelength region. This ensures high darkroom safety, when using longer-wavelength light, already of about 530 nm and above. As a result, a higher degree of safety and an improved quality of the resulting products are achieved, since operations can be visually controlled and working conditions are thus improved. The recording material is thus very suitable for irradiation with argon ion lasers emitting at 514 nm (488 nm) and for use with light sources emitting at similar wavelengths.

Compared with prior art dyes, such as Crystal Violet or Rhodamine FB or Acridine Orange, the sensitizing dye of the present invention causes practically no residual staining.

The sensitizing dyes of the present invention can be prepared as indicated in German Pat. No. 704,141 or U.S. Pat. No. 2,503,776, respectively, or according to an analogous method.

As previously mentioned above, it is possible to use the sensitizing dye of the present invention in combination with other dyes. Combination, for example, with a sensitizing dye corresponding to Formula 3 in the table of formulae can result in an intensive mixed sensitization up to about 600 nm. On the other hand, a dye having the structure indicated in Formula 4, which effects a high and selective sensitization when used alone, produces practically no sensitization, when it is mixed with the sensitizing dye of the present invention.

It is also possible to use mixtures of sensitizing dyes with dyes having their sensitization peaks in the longer-wavelength region, which belong to a different chemical class and do not produce any or only an insignificant sensitization when they are used with silver halide, such as, for example, Acid Green (Acid Green 5, Color Index 42095).

A possibly lower overall sensitivity of the sensitizing dye according to the present invention, compared with systems using, for example, triarylmethane dyes which yield a broader range of sensitization and operating with non-selective sources of light, can be compensated for by the higher light intensity of laser exposure and by a selectively acting sensitization.

The concentration of the sensitizing dye of the present invention in the photoconductive layer depends on the photoconductor used in each individual case, on the desired effect, and also on the sensitizing dyes used. Usually, the sensitizing dye is added in an amount of from about 0.01 to 15% by weight, based on the weight of the photoconductor employed. It is preferred to use from about 0.1 to 1.0% by weight.

If one or several selectively-acting sensitizing dyes are used, there is a possibility, for example, in the production of printed circuits, of using an original consisting of a flat of a printed circuit on a register sheet provided with unicolored or multicolored markings which correspond to the position of the respective sensitization peaks. As a result, these markings or other data are not reproduced. At the same time, it is possible to work in bright safelights, the wavelengths of which correspond to the wavelength of the gap between the sensitivity peaks.

After imaging, developing, removing the photoconductor layer and etching the metal layer in the exposed areas, a printed circuit may be obtained in a known manner.

Charge generation and charge transport in the recording material of the present invention can take place in a single photoconductive layer or in several layers, preferably double layers. These layers comprise photoconductors comprising known organic compounds. Preferably used compounds include oxadiazole derivatives, for example, 2,5-bis-(4'-diethylaminophenyl)-1,3,4-oxadiazole, as described in German Pat. No. 1,058,836 (corresponding to U.S. Pat. No. 3,189,447), or oxazole derivatives, for example, 2-vinyl-4-(2'-chlorophenyl)-5-(4''-diethylaminophenyl)-oxazole, as described in German Pat. No. 1,060,260 (corresponding to U.S. Pat. No. 3,112,197) or in German Pat. No. 1,120,875 (corresponding to U.S. Pat. No. 3,257,203), or 2-phenyl-4-(2'-chlorophenyl)-5-(4''-diethylaminophenyl)-oxazole.

As binders, natural and synthetic resins can be used, which are known for both their adhesive and film-forming properties. Film-forming and electrical properties, as well as adhesion to the support and also solubility characteristics are important when choosing the binders. For printing purposes, binders which are soluble in aqueous or alcoholic solvent systems, preferably with the addition of acid or alkali, are particularly suitable. For physiological and safety reasons, readily inflammable aromatic or aliphatic solvents are undesirable. Accordingly, suitable binders include high-molecular weight substances containing groups which render them alkali-soluble, for example, acid anhydride groups, carboxyl groups, phenol groups, sulfonic acid groups, sulfonamide groups or sulfonimide groups. Copolymers with anhydride groups are particularly useful, since they do not contain any free acid groups and the photoconductive layer therefore has a low dark conductivity, but is nevertheless readily soluble in alkaline media.

The supports used for the recording material may have a planar or cylindrical shape and may comprise a metal plate or a metal foil, metallized papers or metallized plastic films, electrically conductive papers or alternatively, papers or plastic films coated with an electrically conductive plastic material, as is known in the art.

Toner images can be produced in a known manner directly on the recording material of the present invention. It is, however, also possible to transfer either the charge image or the toner image to an image receptor.

The invention will be further illustrated by the following examples with are intended to be illustrative only and in no sense limiting:

EXAMPLE 1

Figure 3:
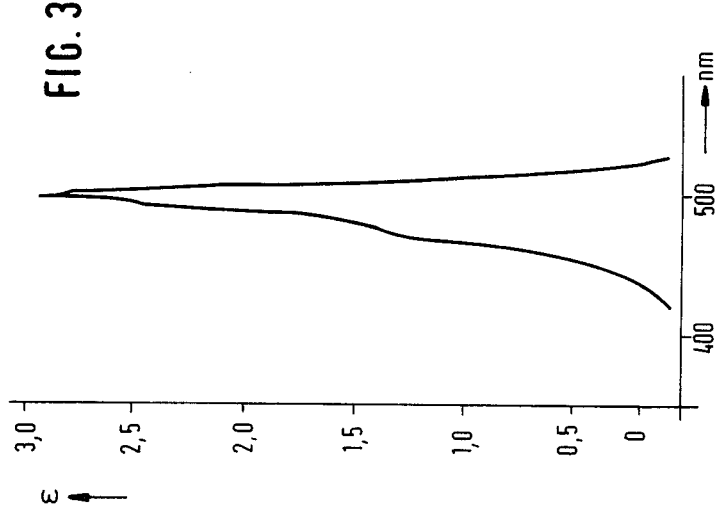
FIG. 3 shows the absorption spectrum of the dye of the present invention indicated under No. 2 in the table of formulae.

A 100 μm thick aluminum foil which had an electrochemically roughened and anodically oxidized surface was coated with a solution comprising 10 g of 2-phenyl-4-(2'-chlorophenyl)-5-(4''-diethylaminophenyl)-oxazole, 15 g of a copolymer of styrene and maleic anhydride having a softening point of 210° C., 116 g of tetrahydrofuran, 33 g of butyl acetate, 76 g of ethylene glycol monomethyl ether, 50 mg (=0.5%, based on the weight of the photoconductor) of the chlorobenzoxazole-trimethine-cyanine sensitizing dye indicated under No. 2 in the table of formulae, having an absorption spectrum as shown in FIG. 3 (measured on an alcoholic solution, 10 mg of dye per liter, diameter 1 cm). After evaporation of the solvent, an approximately 5 μm thick photoconductive layer was obtained.

The photoconductive layer was charged by means of a corona (voltage 5 kV negative, distance 25 mm) and imaged in a conventional automatic machine for the production of printing forms, using an argon ion laser operating in the power range from 0.2 to 0.5 mW (rated power 50 mW, output 15 mW), at a feed of 400 lines/cm, and was thereafter developed with a commercially available electrostatic dry toner.

The printing plate thus obtained has a selective spectral sensitivity with a peak at 505 and 510 nm and a steep drop toward the long-wavelength region of the spectrum, as can be seen from FIG. 1, and it has the advantage that it can be safely handled under safelights.

Figure 2:
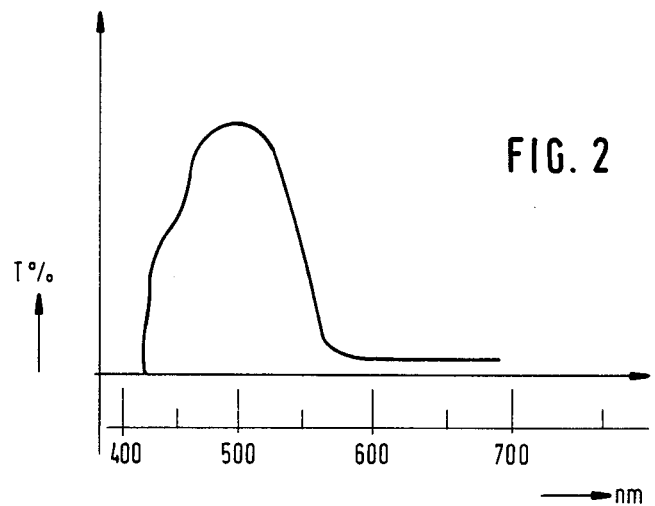
FIG. 2 shows, as a reference, the spectral sensitivity peak of a printing plate produced with the use of a sensitizing dye previously known in the art.

A recording material provided with a photoconductive layer, in which the sensitizing dye of the present invention had been replaced by a comparable amount of Astrazone Orange R (C.I. 48040—cyanine dye) was prepared and imaged as a reference. The spectral sensitization of this reference material is shown in FIG. 2 and its absorption spectrum in FIG. 4. The spectrograms were obtained by exposure to the light of a xenon high-pressure lamp XB0 150 W/1 through a variable interference filter VERIL B-60, No. B 70 776.47, using a gray scale and toner development. A comparison of FIGS. 1, 2, 3 and 4 shows that the sensitization of the reference sample is less selective and the steep drop toward the longer-wavelength region is less strongly pronounced and darkroom safety is thus inferior, compared with the data obtained for the recording material of the present invention.

Figure 4:
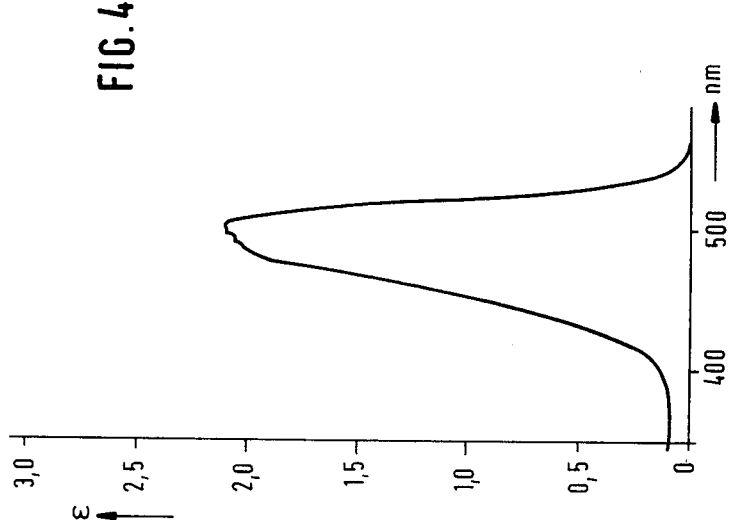
FIG. 4 shows the absorption spectrum of the same reference dye as used in connection with FIG. 2.

Upon exposure to a crypton laser, the spectral sensitivity in $cm^2/Ws$ obtained at the long-wavelength edge of the sensitization spectrum of the sensitizing dye of the present invention (values for Astrazone Orange R indicated in parantheses; spectrograms of FIGS. 2 and 4) has the following values: at 521 nm=4 300 (8000), at 531 nm=2100 (6500), at 545 nm (using a monochromator)=500 (2500).

EXAMPLE 2

A 100 μm thick polyester film which had been vacuum-metallized with aluminum was coated with a solution comprising 15 g of 2,5-bis-(4'-diethyl-aminophenyl)-1,3,4-oxadiazole,
15 g of a copolymer of styrene and maleic anhydride, as indicated in Example 1,
139 g of tetrahydrofuran,
40 g of butyl acetate,
91 g of ethylene glycol monomethyl ether,
30 mg of the sensitizing dye mentioned in Example 1, and
75 mg of the trimethine cyanine dye according to Formula 3.

Figure 5:
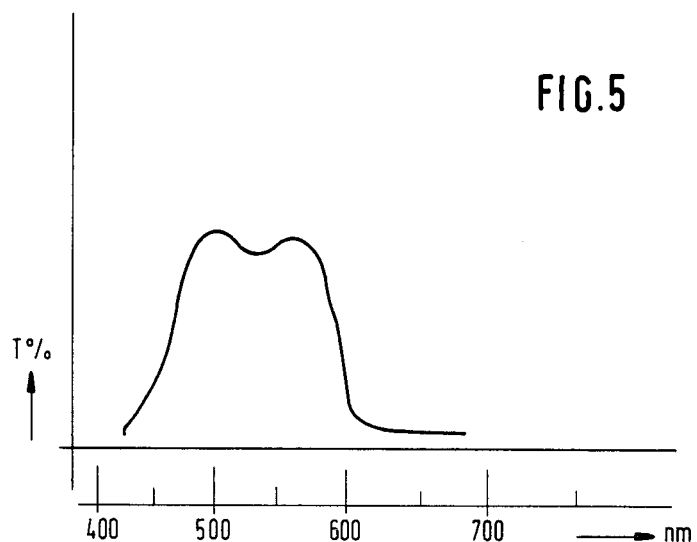
FIG. 5 shows the spectral sensitivity of the electrophotographic recording material prepared in accordance with Example 2 of the present invention.

After evaporation of the solvent, an approximately 5 μm thick photoconductive layer resulted, which had a spectral sensitivity ranging from the short-wave visible region up to about 600 nm, as is shown by FIG. 5.

The film was charged to about −450 V by means of a corona and was then exposed in a reprocamera equipped with 8 autophoto lamps of 500 W each, for 25 seconds. The original used for exposure was the flat of a printed circuit on a register sheet provided with blue and greenish-yellow markings and orientation lines. These markings were not reproduced on the imagewise exposed film due to the light-sensitivity of the photoconductive layer in this spectral region. After developing with an electrophotographic developer and removing the photoconductive layer from the non-image areas, according to the method described in German Pat. No. 2,322,047 (corresponding to U.S. Pat. No. 4,066,453), the uncovered vapor-deposited aluminum layer was removed by treating it with a 2N sodium hydroxide solution. In this manner, a printed circuit was obtained.

EXAMPLE 3

Figure 6:
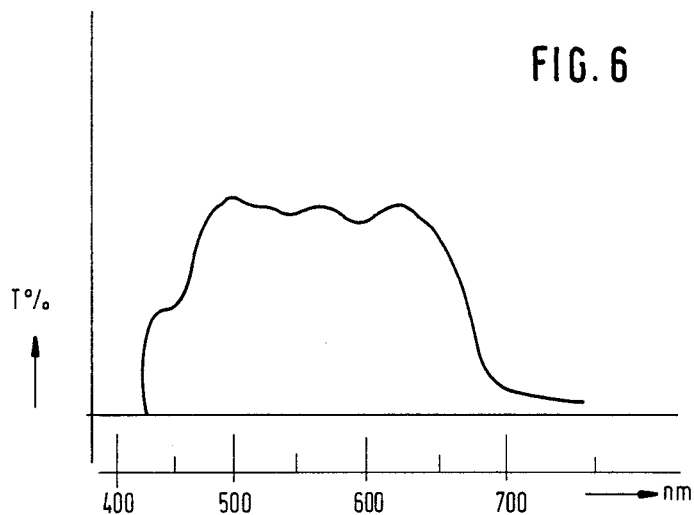
FIG. 6 shows the spectral sensitivity of an electrophotographic recording material produced in accordance with Example 3 of the present invention.

A solution of 8 g of 2-vinyl-4-(2'-chlorophenyl)-5-(4''-diethylaminophenyl)-oxazole and 18 g of a copolymer of styrene and maleic anhydride, as indicated in Example 1, in a mixture of 90 g of ethylene glycol monomethyl ether, 140 g of tetrahydrofuran and 40 g of butyl acetate, 85% strength, is admixed with 24 mg of the sensitizing dye indicated under No. 2 in the table of formulae, 40 mg of the sensitizing dye according to Formula 3, and 64 mg of Acid Green (C.I. 42095, Acid Green 5). The solution is applied to an aluminum foil which has an electrochemically roughened and anodically oxidized surface and has been pre-treated with polyvinylphosphonic acid, as described in German Offenlegungsschrift No. 1,621,478 (corresponding to U.S. Pat. No. 4,153,461). After evaporation of the solvent, a layer is obtained, which has a photosensitivity ranging from the short-wave visible region of the spectrum up to about 660 nm, which, on the one hand, shows a good utilization of the source of light employed and, on the other hand, makes it possible, to work in visible red light so that the operations can be visually controlled (FIG. 6).

The following method is used to produce a printing form for offset printing from this recording material: The photoconductive layer is charged in the dark to −430 V, with the aid of a corona and is then exposed in a reprocamera, for 10 seconds, at aperture f/14, using 10 metal halide lamps having an output of 600 W each as the source of light. The resulting latent charge image is developed with a commercially available dry toner applied by means of a magnetic roll and the toner image is fixed by heating. The photoconductive layer is removed from the areas which are not covered by toner, with a solution prepared by dissolving 50 g of $Na_2SiO_3.9H_2O$ in 250 g of glycerol (86% strength) and diluting with 390 g of ethylene glycol and 310 g of methanol. As a result, a planographic printing form is obtained, which can be used to produce a large print run.

What is claimed is:

1. An electrophotographic recording material, comprising:
    an electrically conductive support layer, and at least one photoconductive layer applied thereto which comprises (a) an organic photoconductor selected from the group consisting of an oxadiazole, an oxazole photoconductor, and derivatives thereof, (b) at least one sensitizing dye, and (c) a binder, wherein the sensitizing dye contained in the photoconductive layer comprises a compound corresponding to the formula:

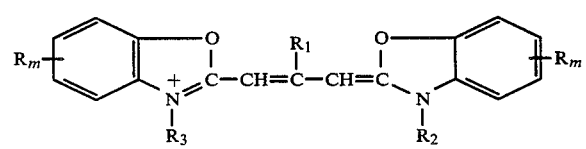

wherein

R is chlorine or bromine, m is 1 or 2, $R_1$ is an alkyl group having from 1 to 3 carbon atoms, $R_2$ is —$(CH_2)_n$—$SO_3H$ or —$(CH_2)_2$—COOH, $R_3$ is —$(CH_2)_n$—$SO_3^-$ or —$(CH_2)_2$—$COO^-$ and n is 3 or 4.

2. A recording material as claimed in claim 1, wherein the sensitizing dye contained in the photoconductive layer comprises a compound corresponding to the following formula:

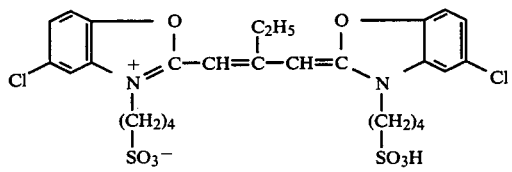

3. A recording material as claimed in claim 1, wherein the photoconductive layer further comprises a second sensitizing dye having a sensitivity peak which is shifted by more than about 60 nm in the longer-wavelength direction from the sensitivity peak of the first sensitizing dye.

4. A recording material as claimed in claim 3, further comprising a second sensitizing dye contained in the photoconductive layer, which second sensitizing dye comprises a compound corresponding to the following formula

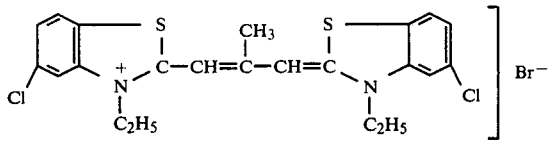

5. A recording material as claimed in claim 1, wherein the photoconductive layer further comprises Acid Green (Color Index 42095) as a sensitizing dye.

6. A recording material as claimed in claim 3, wherein the region inbetween the two sensitivity peaks comprises a greatly reduced sensitivity.

7. A recording material as claimed in claim 1, wherein the sensitizing dye comprises from about 0.1 to 15% by weight of the photoconductor.

8. A recording material as claimed in claim 1, wherein the sensitizing dye comprises from about 0.1 to 1% by weight of the photoconductor.

9. A recording material as claimed in claim 1, wherein the organic photoconductor is contained in two photoconductive layers.

10. A recording material as claimed in claim 1, wherein said material comprises an acute sensitivity peak at from about 505 to 510 nm.

11. A recording material as claimed in claim 1, wherein said binder comprises copolymers with anhydride groups.

12. A recording material as claimed in claim 1, wherein said material exhibits a selective spectral sensitivity peak comprising a steep drop toward the long wavelength direction.

13. A recording material as claimed in claim 1, wherein said photoconductive layer is about 5 μm thick.

* * * * *